United States Patent [19]

Webb

[11] Patent Number: 4,486,607

[45] Date of Patent: Dec. 4, 1984

[54] PROCESS FOR THE PRODUCTION OF PHENYL SUBSTITUTED PROPANAL

[75] Inventor: David Webb, Brentwood, England

[73] Assignee: Bush Boake Allen Limited, London, England

[21] Appl. No.: 397,164

[22] Filed: Jul. 12, 1982

Related U.S. Application Data

[63] Continuation of Ser. No. 202,608, Oct. 31, 1980.

[30] Foreign Application Priority Data

Jul. 9, 1980 [GB] United Kingdom ............... 8022381

[51] Int. Cl.$^3$ .................... C07C 45/00; C07C 29/34; C07C 29/44
[52] U.S. Cl. .................... 568/425; 568/814; 568/715
[58] Field of Search ............... 568/814, 715, 425, 628

[56] References Cited

U.S. PATENT DOCUMENTS

| | | | |
|---|---|---|---|
| 2,184,526 | 12/1939 | Meuly | 568/814 X |
| 2,737,536 | 3/1956 | Bloch et al. | 568/715 X |
| 2,875,131 | 2/1959 | Carpenter et al. | 568/425 X |
| 3,110,747 | 11/1963 | Mullineaux | 568/814 X |
| 3,280,192 | 10/1966 | Levy et al. | 568/814 X |
| 3,548,006 | 12/1970 | Scriabine | 568/425 |

FOREIGN PATENT DOCUMENTS 0009239  2/1980  European Pat. Off. .

OTHER PUBLICATIONS

Groggins, Unit Processes in Organic Synthesis, (1952), 799, 814.
Khalaf (I), Revue Roumaine de Chemie, vol. 19, (1974), 1373–1380.
Khalaf (II), Indian Journal of Chemistry, vol. 12, (1974), 476–480.
Khalaf (III), Jour. of Org. Chem., vol. 34, No. 11, (1969), 3571–3573.

*Primary Examiner*—Bernard Helfin

[57] ABSTRACT

The invention relates to a process for the production of 3 (alkyl phenyl) propanals; certain of which are known to be valuable in the perfumery industry. The process enables this group of chemicals to be produced more easily as compared to known processes for their production. In a preferred embodiment in one step of the process the alkylation of the 3 phenyl propanol is carried out under controlled conditions so as to favor the production of para isomer of the product.

16 Claims, No Drawings

PROCESS FOR THE PRODUCTION OF PHENYL SUBSTITUTED PROPANAL

This is a continuation of application Ser. No. 202,608 filed Oct. 31, 1980.

This invention relates to processes for the production of certain phenyl substituted propanals.

The preparation and odiferous properties of a number of phenyl substituted propanals of the general formula:

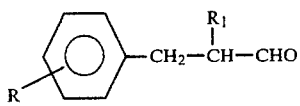

wherein R represents an alkyl group having from 1 to 5 carbon atoms and $R^1$ represents a hydrogen atom or a methyl group has been reviewed by Berends and van der Linde. (Perfumery and Essential Oil Record June 1967 p372-378). Of the aldehydes which he prepared those wherein R represents an isopropyl or a tertiary butyl group have become articles of commerce by virtue of their utility as ingredients of compounded perfumery compositions. The compound where R represent a para tertiary butyl group and $R^1$ represents a methyl group is particularly valuable in this respect. These aldehydes are synthetic organic chemicals which have not been found in nature. Because of their known value the industry has devoted a good deal of effort to devising synthetic methods whereby these aldehydes can be manufactured more cheaply and efficiently. Besides those methods which are reviewed by Berends and vander Linde a number of other synthetic techniques have recently been proposed see for example U.S. Pat. No. 4,070,374 and British Patent Application No. 2009151.

We have now discovered a novel process whereby certain of the aldehydes having the general formula described above can be prepared in high yield and at low cost. From one aspect our invention provides a process for the manufacture of an aldehyde having the formula I.

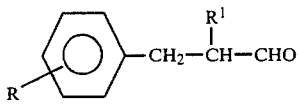

wherein R represents a secondary or tertiary alkyl group having 3 or 4 carbon atoms and $R^1$ represents a hydrogen atom or a methyl group which comprises reducing an aldehyde which is 3-phenyl prop-2-enal or 3 phenyl 2-methyl prop-2-enal to the corresponding 3 phenyl propanol, alkylating said phenyl propanol with an appropriate alkylating agent so as to produce a product comprising a 3-(mono alkyl phenyl) propanol wherein the alkyl group is a secondary or tertiary alkyl group comprising 3 or 4 carbon atoms and oxidising said 3-(mono alkyl phenol) propanol so as to produce the corresponding propanal.

In a preferred embodiment the invention provides a process for the manufacture of a compound having the formula I, wherein the substituent R is in the para position on the aromatic ring.

The aldehyde starting material may conveniently be produced by the condensation of benzaldehyde and propionaldehyde or acetaldehyde which is an example of an aldol condensation and can be carried out using any of the reaction techniques which are known per se to be useful for this reaction. By the term "reaction techniques known per se" in the specification is meant techniques for the reaction which are or have been used or described in the chemical literature. Thus the propionaldehyde or acetaldehyde may be added to a stirred solution of benzaldehyde in a suitable solvent e.g. an aqueous solution of an aliphatic alcohol such as methanol in the presence of a suitable basic catalyst e.g. sodium hydroxide. The reactants are preferably maintained at a temperature in the range 20° to 80° C. for a period of up to 3 hours. The reaction is normally carried out using at least a molar excess of benzaldehyde so as to minimise by-product formation. The reaction products may be separated using conventional techniques e.g. fractional distillation. The separation of the 3-phenyl prop-2-enal is a strongly preferred. The preferred aldehyde for present use is propionaldehyde the preferred products being those wherein $R_1$ represents a methyl group.

The product aldehyde may be reduced to the corresponding alcohol using the reaction techniques for such a type of reduction known per se Conveniently, the reduction can be carried out by the catalytic hydrogenation of the aldehyde. This hydrogenation may be effected in the presence of a suitable catalyst e.g. copper chromite at a temperature of from 120° to 180° C. and a pressure of 100 to 150 p sig. hydrogen. Once the uptake of hydrogen has ceased the reaction mixture is filtered and the desired alcohol separated by distillation.

In a second aspect the present invention provides a process for the manufacture of a 3-(alkyl phenyl) propanol i.e. one having the formula:

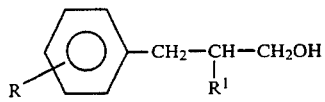

wherein R and $R^1$ are as defined above, which process comprises alkylating in the presence of an electrophilic catalyst a 3-phenyl propanol with an alkylating agent so as to produce a product comprising said 3-(alkyl phenyl) propanol.

The introduction of an alkyl substituent into an aromatic compound may be achieved by Friedel Crafts reaction e.g. reaction with an alkylating agent in the presence of an electrophilic catalyst.

The alkylating agents and catalysts which are useful in the processes of our invention can conveniently be considered as falling into two distinct groups. The first group comprises alkylating agents which are secondary or tertiary alkyl halides having 3 or 4 carbon atoms and catalysts which are Lewis acids such as aluminium chloride, ferric chloride and zinc chloride.

The second group comprises alkylating agents which are alkenes or secondary or tertiary alkanols having 3 or 4 carbon atoms or oligomers of such alkenes and catalysts which are protonic acids.

The product of the alkylation may comprise a mixture of dialkylated and monoalkylated species and isomers thereof together with any unreacted starting materials. The relative proportions of these various possible products which are formed varies with the nature of the reactants, and catalyst and according to the conditions under which the alkylation is carried out. We have found that it is possible to influence the proportion of the various possible alkylated products by specific choice of the reaction conditions.

In the case of the first group of alkylating agents the choice and volume of the solvent, the mode of addition of the reactants and catalyst, the molar ratio of the reactants and their concentration can all exert an appreciable effect upon the composition of the product although in general less than that exerted by the nature of reactants and the particular catalyst which is used. Nevertheless, the particular conditions under which the reaction is carried out may well make a significant difference to the composition of the desired product.

The preferred alkyl halide alkylating agents for present use are chlorides especially tertiary butyl chloride and isopropyl chloride. The preferred Lewis acid catalysts are aluminium chloride and ferric chloride.

Using this alkylating system the reaction is preferably carried out by mixing the halide and the primary alcohol and adding the resulting mixture to a solution or suspension of the catalyst. The solvent may be any of those known for use in Friedel Crafts alkylations e.g. nitrobenzene or carbon disulphide. Preferably ethylene dichloride or di-chloromethane is employed as the solvent. The temperature of the reactants is preferably maintained within the range—30° to 40° C. The utilisation of lower temperatures appears to increase the proportion of para to meta alkylated product, but in general the lower the temperature the lower degree of conversion of the starting material, so in the preferred embodiment of this invention where the aim of the alkylation is the production of the para substituted product the temperature employed will be selected so as to achieve a compromise.

The phenyl propanol and the alkyl chloride will normally be employed in approximately equimolar quantities. Larger proportions of phenyl propanol will favour the selective formation of a para substituted products but the use of such excesses is less preferred because of the consequent lower degree of conversion. The Lewis acid catalysts may be employed in any convenient quantity but in general we prefer to use from 0.3 to 1.0 moles most preferably 0.4 to 0.6 moles of catalyst per mole of phenyl propanol. Preferably a volume of solvent which is from 1 to 6 times the total volume of the reactants is employed. The use of a larger volume of solvent appears to favour the selective formation of a para substituted product but this is in general uneconomic and we prefer to employ a volume of solvent which is from 2 to 5 times the volume of the reactants.

The product mixture may be allowed to warm to ambient temperature if appropriate, at the end of the reaction and is then washed and dried.

The product mixture can be separated from any unchanged starting material using conventional techniques e.g. fractional distillation.

The particular technique for the alkylating procedures of this invention using the second group of alkylating agents and catalysts varies with the particular nature of the alkylating agent. The preferred alkenes for use according to our invention are propylene and isobutylene which are gases at the temperatures at which the processes will be carried out. The preferred technique for operating an alkylating process involving the use of gaseous alkene is to bubble the gas through a liquid medium comprising the other reactants.

The alcohols useful to our invention are in essence those which are dehydrated and protonated in situ to generate an appropriate carbonium ion. Preferred alcohols for present use are isopropanol, and tertiary butanol. These alcohols are preferably added in small increments to the reaction medium as the reaction progresses.

The preferred oligomeric alkenes for present use are di-isobutylene (a mixture of 2,4,4 trimethyl pent-1-ene and 2,4,4 trimethyl pent-2-ene) and tri-isobutylene (a mixture of dodecanes consisting predominantly of 2,4,4,6,6 pentamethyl-hept-1-ene). Alkylation processes using these oligomers as the alkylating agents are preferably carried out at a temperature below the boiling point of the oligomer so that the liquid oligomer can be gradually added to the other reactants during the alkylation reaction.

Any acid which is sufficiently strong to protonate the alkylating agent and thereby generate an appropriate carbonium ion can be used to catalyse the reaction. However, acids which react chemically and irreversibly with the primary phenyl substituted alcohol should not be employed. The preferred catalyst for present use is phosphoric acid. The use of a concentrated acid i.e. at least 85% and preferably at least 90% acid being especially preferred.

The alkylation reaction proceeds more rapidly and with greater conversion of the starting material as more acid is employed. A strong acid catalyst is preferably employed in a quantity of from 1 to 5 times more preferably 2 to 3 times the weight of the phenyl substituted alcohol.

The reaction medium is preferably maintained at a temperature of from 50° to 150° C. more preferably from 60° to 100° say 60° to 80° C. When using higher temperatures within these ranges e.g. 100° to 150° C. particular attention should be paid to any possible reaction between the protonic acid and the primary alcohol. At lower temperatures the rate of oligomerisation of the alkylating agent becomes more significant. Because of this tendency it is preferred to terminate the reaction before all the phenyl propanol has been converted e.g. at 50 or 60% conversion. Where oligomeric alkenes are employed as the alkylating agent a higher temperature e.g. 90° to 120° C. is preferably employed.

The desired mono-alkyl phenyl substituted alcohol is preferably separated from the reaction product of the alkylation reaction prior to the final oxidation step. This separation may conveniently be effected by fractional distillation. If this fractionation is carried out sufficiently carefully, it is possible where appropriate to obtain a fraction which is rich in the para substituted product and a second fraction which is correspondingly rich in the meta substituted product.

The alkylation product comprises a mixture of the meta and para isomers of the product. Mixtures which comprise at least 3% of the meta isomer are believed to be novel. Thus from another aspect our invention provides a mixture of the meta and para isomers of a 3 alkyl phenyl) propanol as hereinbefore defined which comprises from 50 to 97% preferably from 80 to 97% of the para isomer. Mixtures of the corresponding aldehydes obtained by oxidation of alkylation product are also believed to be novel.

The final oxidation step may be carried out by using reaction techniques of oxidation or dehydrogenation known perse for this type of oxidation or dehydrogenation. We prefer to dehydrogenate the alcohol in the presence of a suitable catalyst such as Raney nickel, Raney copper or most preferably copper chromite. This reaction may be effected by adding the alcohol to a stirred suspension of the catalyst in a suitable nonvolatile solvent which is maintained at a temperature in the range 100° to 220° C. and at a subatmospheric pressure. The temperature and pressure are selected so as to arrange that the desired aldehyde product is fractionally distilled from the reaction medium as it is formed which arrangement minimises by-product formation. The invention is illustrated by the following Examples:

EXAMPLE 1

Preparation of α-Methylcinnamaldehyde

Propionaldehyde (87 gms 15 moles) was added at 50° C. over a period of 5 hours to a stirred mixture of benzaldehyde (318 gms, 3 moles), methanol (500 mls), water (500 mls) and sodium hydroxide (25 gms). After a further 1 hour stirring at 50° C., the reaction mixture was brought to neutrality with acetic acid and the methanol fractionated out of the reaction. The organic layer was then separated from the aqueous layer and fractionated to recover the excess of benzaldehyde (109 gms, b.pt. 36°–40° C./2 mm Hg) and obtain the -methylcinnamaldehyde (167 gms, b.pt. 100°–102° C./2 mm).

EXAMPLE 2

Preparation of 2-methyl-3-phenylpropanol

α-methylcinnamaldehyde was hydrogenated using copper chromite (2% by weight) as catalyst at a temperature of 150° C. and a pressure of 130° C. psig hydrogen. After the uptake of hydrogen ceased, the mixture was filtered and distilled to obtain the 2-methyl-3-phenylpropanol (b.pt 100° C./1 mm).

EXAMPLE 3

Reaction of t-butyl chloride with 2-methyl-3-phenylpropan-1-ol

A mixture of t-butyl chloride (0.5 moles) and 2-methyl-3-phenylpropanol (0.5 moles) was added over a period of 60 minutes to a stirred mixture of anhydrous ferric chloride (0.5 moles) and dichloromethane (400 mls), maintaining the temperature between 0° C. and 5° C. The reaction mixture was then stirred for a further 5.5 hrs. at this temperature after this period, the ferric chloride was washed out of the reaction with water and then with dilute sodium hydroxide solution. Distillation of the organic layer yielded 90 gms of a product (b.pt 100°–140° C./2 torr) which on analysis by gas liquid chromatography, was found to contain 21 gms of starting material, 9 gms. of the meta-alkylated product, 53.5 gms. of the para-alkylated product and 6.5 gms of the disubstituted product.

EXAMPLE 4

Reaction of isobutylene with 2-methyl-3-phenyl propan-1-ol

Over a period of 12.5 hours, 114 gms of isobutylene was bubbled into a stirred mixture of 285 gms of 2-methyl-3-phenylpropan-1-ol and 750 gms of phosphoric acid (90% w/w). The temperature was maintained at 70° C. After this time, the reaction mixture was diluted with ethylbenzene and the phosphoric acid washed out, initially with water and then with dilute sodium hydroxide solution. Distillation of the organic layer yielded 306 gms of a product (b.pt. 100°–140° C./2 torr) which was found to contain (by gas liquid chromatography) 137 gms of starting material, 149 gms of the para alkylated product and 11 gms. of the meta alkylated product.

EXAMPLE 5

Preparation of 3-(t-Butylphenyl)-2-methylporpanaldehyde 3-(t-Butylphenyl)-2-methylpropan-1-ol (95% p 5% m) was added continously to a stirred mixture of copper chromite and liquid paraffin (the mixture containing about 5% by weight of copper chromite) at a temperature of 180° C. and a pressure of 2 mms Hg. The required aldehyde was slowly fractionated out from the reaction mixture as a mixture of 95% of the para substituted alcohol and 5% of the meta substituted alcohol.

EXAMPLE 6

Preparation of 3-(t-butylphenyl)-2-methyl-propanol 150 grams of 3-phenyl-2-methyl-propanol and 375 grams of 90% aqueous phosphoric acid were heated to 100° C. and 56 grams of di-isobutylene were added with stirring over a period of 45 minutes. The temperature was maintained at 100° C. for 5.5 hours and thereafter at 110° C. for a period of 6 hours. The product was cooled and the organic layer separated washed three times with water and once with dilute KOH. The product was distilled through a 6 inch vigreaux column to give 124 grams of a product (B.Pt 110°–150° C./4$_t$) which was analysed to GLC and found to be 3-(t-butylphenyl)-2-methyl-propanol (49.1%) (44.8% para isomer and 4.3% meta isomer).

I claim:

1. A process for the preparation of a 3(alkylphenyl) propanol having the formula:

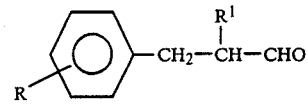

wherein R represents a secondary or tertiary alkyl group having 3 or 4 carbon atoms and $R^1$ represents a hydrogen atom or a methyl group which comprises:
(i) reducing an aldehyde which is 3-phenyl-prop-2-enal or 3-phenyl-2-methyl-prop-2-enal to produce the corresponding 3-phenyl propanol;
(ii) reacting said 3-phenyl propanol in concentrated phosphoric acid of at least 85 percent concentration with an alkylating agent selected from the group consisting of alkanols and alkenes having 3 or 4 carbon atoms and oligomers of such alkenes so as to produce a product comprising a 3-(mono alkyl phenyl) propanol wherein the alkyl group is a secondary or tertiary alkyl group comprising 3 or 4 carbon atoms, and
(iii) oxidizing said 3(-mono alkyl phenyl) propanol so as to produce a 3-(monoalkylphenyl) propanol.

2. A process according to claim 1, wherein the oxidation of the 3 (monoalkyl phenyl) propanol is carried out by catalytic dehydrogenation.

3. A process according to claim 1, wherein the catalyst is selected from the group consisting of Raney nickel, Raney copper and copper chromite.

4. A process according to claim 1 in which the alkylation agent is selected from the group consisting of alkanols and alkenes having 3 or 4 carbon atoms or oligomers of such alkenes and the reaction (ii) is performed in concentrated phosphoric acid of at least 85 percent concentration present in an amount of from 1 to 5 times the weight of the 3-phenylpropanal.

5. A process according to claim 1 in which the alkylating agent is propylene or isobutylene and the reaction (ii) is performed by bubbling the propylene or isobutylene through a liquid medium comprising the propanol and concentrated phosphoric acid of at least 85 percent concentration.

6. A process according to claim 1 in which the alkylating agent is tertiary butanol or diisobutylene and the reaction (ii) is conducted in concentrated phosphoric acid of at least 85 percent concentration.

7. A process according to claim 1 in which the reaction (ii) is carried out by heating the reaction mixture to a temperature of 50° to 150° C.

8. A process according to claim 1 in which the reaction (ii) is carried out by reacting isobutylene with the 3-phenylpropanol in the presence of from 1 to 5 times the weight of the 3-phenylpropanol of phosphoric acid of at least 85% concentration and at a temperature of from 60° to 100° C.

9. A process according to claim 1 wherein $R_1$ represents a methyl group.

10. A process for the production of 3-alkylphenylpropanol having the formula:

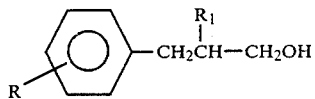

wherein R represents a secondary or tertiary alkyl group having 3 or 4 carbon atoms and $R_1$ represents a hydrogen atom or a methyl group, which comprises; reacting a 3-phenylpropanol with an alkylating agent, selected from $C_{3-4}$ alkenes, $C_{3-4}$ secondary or tertiary alcohols and oligomers of $C_{3-4}$ alkenes, in the presence of concentrated phosphoric acid of at least 85 percent concentration.

11. A process according to claim 10 in which the amount of phosphoric acid is 1 to 5 times, by weight, the amount of the propanol.

12. A process according to claim 10 in which the alkylating agent is propylene or isobutylene and the reaction is performed by bubbling the propylene or isobutylene through a liquid medium comprising the propanol and the acid.

13. A process according to claim 10 in which the reaction is carried out by heating the reaction mixture to a temperature of 50° to 150° C.

14. A process according to claim 10 and which is carried out by reacting isobutylene with 3-phenylpropanol in the presence of from 1 to 5 times the weight of propanol of phosphoric acid of at least 85% concentration and at a temperature of 60° to 100° C.

15. A process according to claim 10 in which the concentration of phosphoric acid is at least 90%.

16. The process of claim 1 wherein the concentration of phosphoric acid is at least 90 percent.

* * * * *